(12) United States Patent
Kim et al.

(10) Patent No.: US 9,714,453 B2
(45) Date of Patent: Jul. 25, 2017

(54) METHOD FOR DETECTING GENES SENSITIVE TO LOW-LEVEL IONIZING RADIATION

(71) Applicant: KOREA HYDRO & NUCLEAR POWER CO., LTD., Gyeongju-Si, Gyeongsangbuk (KR)

(72) Inventors: Hee Sun Kim, Uijeongbu (KR); Seung Jin Choi, Seoul (KR); Moo Hyun Choi, Seoul (KR); Jin Jong Bong, Seoul (KR); Seok Cheol Shin, Seoul (KR)

(73) Assignee: KOREA HYDRO & NUCLEAR POWER CO., LTD., Gyeongju-Si (KR)

( * ) Notice: Subject to any disclaimer, the term of this patent is extended or adjusted under 35 U.S.C. 154(b) by 0 days.

(21) Appl. No.: 15/346,680

(22) Filed: Nov. 8, 2016

(65) Prior Publication Data
US 2017/0058358 A1    Mar. 2, 2017

Related U.S. Application Data

(62) Division of application No. 14/399,954, filed as application No. PCT/KR2012/003928 on May 18, 2012, now Pat. No. 9,512,489.

(30) Foreign Application Priority Data

May 10, 2012 (KR) ......................... 10-2012-0049544

(51) Int. Cl.
C12Q 1/68    (2006.01)

(52) U.S. Cl.
CPC ......... *C12Q 1/6886* (2013.01); *C12Q 1/6883* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 2002/0009738 A1 | 1/2002 | Houghton et al. |
| 2009/0208939 A1 | 8/2009 | Flores et al. |

FOREIGN PATENT DOCUMENTS

| JP | 9-501936 | 2/1997 |
| JP | 2004-505611 A | 2/2004 |
| JP | 2008-537474 A | 9/2008 |
| KR | 10-0541529 B1 | 1/2006 |
| KR | 10-0957055 B1 | 5/2010 |
| WO | 95/05853 A1 | 3/1995 |
| WO | 2011073629 A2 | 6/2011 |

OTHER PUBLICATIONS

Shin et al., "Differential expression of immune-associated cancer regulatory genes in low-versus high-dose-rate irradiated AKR/J mice", Genomics, Jun. 2011, vol. 97, No. 6, pp. 358-363.
NCBI GenBank Accession No. NM_010570.1, Jan. 25, 2000.
NCBI GenBank Accession No. NM_011400.1, Aug. 3, 2002.
NCBI GenBank Accession No. NM_009204.1, Jan. 4, 2000.
NCBI GenBank Accession No. NM_009204.1, Jan. 7, 2002.
NCBI GenBank Accession No. NM_013631.1, Jun. 10, 2000.
NCBI GenBank Accession No. NM_008061.1, Jan. 4, 2000.
Shin et al., "Life Span and Lymphoma Incidence in High- and Low-Dose-Rate Irradiated AKR/J Mice and Commonly Expressed Genes," Radiation Research, Jun. 2, 2010, pp. 341-346, vol. 174, No. 3.
Parle-McDermott et al., "Serial analysis of gene expression identifies putative metastasis-associated transcripts in color tumour cell lines," British Journal of Cancer, 2000, pp. 725-728, vol. 83, No. 6.
Iwakawa et al., "Mouse Research Models for Individual Radiosensitivity—Individual Variance and Strain Variance," Jpn Soc. Ther. Radiol. Oncol., 2005, pp. 141-147, vol. 17.
Ishikawa et al., "Onset of Thymic Leukemia in AKR/J and AKR/cum mice," Journal of Japan Society of the Reticuloendothelial System, 1982, pp. 44, vol. 22, No. 1.
Gen Bank Accession No. NM_010570.4, GI: 161086993, publicly available May 14, 2011.
GenBank Accession No. NM_011400.3, GI: 165377225, publicly available May 14, 2011.
GenBank Accession No. NM_009204.2, GI: 118026924, publicly available May 14, 2011.
GenBank Accession No. NM_013631.2, GI: 153792130, publicly available May 14, 2011.
NM_008061.3, GI: 118131011, publicly available May 14, 2011.
Pusztai and Hess, "Clinical trial design for microarray predictive marker discovery and assessment," Annals of Oncology, 2004, pp. 1731-1737, vol. 15.

*Primary Examiner* — Jennifer Dunston
(74) *Attorney, Agent, or Firm* — IM IP Law; C. Andrew Im

(57) ABSTRACT

A method for detecting genes sensitive to low-level ionizing radiation and genes detected by the method. More specifically, genes sensitive to low-level ionizing radiation, discovered in a carcinogenic entity and verified in a normal entity are detected by subjecting a cancerous AKR/J mouse and a normal ICR mouse to low-level radiation. Thymus is collected therefrom, and glycometabolism-related genes are classified via microarray processing of the thymus. The genes are amplified and the levels of gene expression are measured. Thus, a gene having a specific reaction to radiation can be accurately detected by preventing the interference of confounding variables.

4 Claims, 2 Drawing Sheets

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: IRS1 Forward Primer

<400> SEQUENCE: 1
ggtgcagcag atctggataa                                                     20

<210> SEQ ID NO 2
<211> LENGTH: 20
<212> TYPE: DNA
<213> ORGANISM: Artificial Sequence
<220> FEATURE:
<223> OTHER INFORMATION: IRS1 Backward Primer

<400> SEQUENCE: 2
ggtcttctga tgggaaatgg                                                     20

<210> SEQ ID NO 3
<211> LENGTH: 20
<212> TYPE: DNA
<213> ORGANISM: Artificial Sequence
<220> FEATURE:
<223> OTHER INFORMATION: Glut1 Forward Primer

<400> SEQUENCE: 3
atcttcgaga aggcaggtgt                                                     20

<210> SEQ ID NO 4
<211> LENGTH: 20
<212> TYPE: DNA
<213> ORGANISM: Artificial Sequence
<220> FEATURE:
```

```
<223> OTHER INFORMATION: Glut1 Backward Primer

<400> SEQUENCE: 4
acaaacagcg acaccacagt                                              20

<210> SEQ ID NO 5
<211> LENGTH: 20
<212> TYPE: DNA
<213> ORGANISM: Artificial Sequence
<220> FEATURE:
<223> OTHER INFORMATION: Glut4 Forward Primer

<400> SEQUENCE: 5
agagagcgtc caatgtcctt                                              20

<210> SEQ ID NO 6
<211> LENGTH: 20
<212> TYPE: DNA
<213> ORGANISM: Artificial Sequence
<220> FEATURE:
<223> OTHER INFORMATION: Glut4 Backward Primer

<400> SEQUENCE: 6
acagcattga tgcctgagag                                              20

<210> SEQ ID NO 7
<211> LENGTH: 20
<212> TYPE: DNA
<213> ORGANISM: Artificial Sequence
<220> FEATURE:
<223> OTHER INFORMATION: LPK Forward Primer

<400> SEQUENCE: 7
tgatcactaa ggctcgacca                                              20

<210> SEQ ID NO 8
<211> LENGTH: 20
<212> TYPE: DNA
<213> ORGANISM: Artificial Sequence
<220> FEATURE:
<223> OTHER INFORMATION: LPK Backward Primer

<400> SEQUENCE: 8
ggtctctcca gacagcatga                                              20

<210> SEQ ID NO 9
<211> LENGTH: 20
<212> TYPE: DNA
<213> ORGANISM: Artificial Sequence
<220> FEATURE:
<223> OTHER INFORMATION: G6pc Forward Primer

<400> SEQUENCE: 9
tcctctttcc catctggttc                                              20

<210> SEQ ID NO 10
<211> LENGTH: 20
<212> TYPE: DNA
<213> ORGANISM: Artificial Sequence
<220> FEATURE:
<223> OTHER INFORMATION: G6pc Backward Primer

<400> SEQUENCE: 10
tccacttgaa gacgaggttg                                              20
```

METHOD FOR DETECTING GENES SENSITIVE TO LOW-LEVEL IONIZING RADIATION

RELATED APPLICATIONS

This application is a continuation of application Ser. No. 14/399,954 filed Nov. 9, 2014, which is a §371 application from PCT/KR2012/003928 filed May 18, 2012, which claims priority from Korean Patent Application No. 10-2012-0049544 filed May 10, 2012, each of which is herein incorporated by reference in its entirety.

TECHNICAL FIELD

The present invention relates to a method for detecting genes sensitive to a low level of ionizing radiation and genes detected by the method, and more particularly, to a method for detecting genes sensitive to a low level of ionizing radiation, the method including irradiating cancer-induced mice and normal mice with a low level of radiation, and screening glucose metabolism-related genes, which are observed commonly in the normal mice and the cancer-induced mice, from the thymi of the mice.

BACKGROUND ART

With an increase in the industrial and medical use of radiation, various studies on the effects of radiation on the human body have been conducted, and particularly, cancer therapy with radiation has received attention. It is known that high doses of ionizing radiation cause DNA damage, genetic modification, and diseases, including cancer, but a radiation dose of 200 mGy or less and a radiation dose rate of 6 mGy/hr or less inhibit cancer development by activating immune responses.

In general, studies on the relationship between radiation and cancer development, particularly gene responses to radiation, have been conducted, but confounding factors have significantly affected the results to reduce the reliability of the results. However, most studies conducted to date could not explain various responses, which occur in the cells, tissues and organs of the body in the body stage, because these studies were performed using gene-modified cell lines or cancer cell lines. In other words, because gene responses were evaluated using general mice, a variety of genes were expressed, and because cancer development was not limited to a specific organ, it was difficult to analyze gene responses.

In prior art methods that use cells for cancer research, genes were modified, or cancer cells lacking p53 that is important in cancer development were irradiated. For this reason, there was a problem in that the results could not be applied to individuals, because they did fundamentally differ from the responses of normal cells. To overcome this problem, studies on the effects of radiation on cancer development have been conducted using mice having a gene similarity of 95% or more with humans. However, cancer incidence in general mice is very low, and thus a variety of mouse models for cancer research have been used.

In prior studies, a variety of methods were used to screen glucose metabolism-related genes sensitive to a low level (0.7 mGy/hr) of radiation. However, genes disclosed in the present invention are not yet known as genes sensitive to a low level (0.7 mGy/hr) of radiation. Technologies prior to the identification of the profile of genes according to the present invention are as follows.

(1) Cancer cells are characterized by activating glucose uptake and glycolysis (Warburg O, Science 1956; 123: 309-314).

(2) Activated glucose metabolism inhibited p53 activity in thymus, inhibited puma induction, affected the balance between the expression of Bcl2 family proteins and the inhibition of apoptosis, and maintained cancer survival (Zhao Y et. al., J Biol Chem 2008; 283: 36344-36353).

(3) Apoptosis increased in the ileum of Akt1 knockdown mice irradiated with ionizing radiation (Plastaras et al., 2008).

Accordingly, the present inventors have identified the profile of glucose metabolism-related genes sensitive to a low level of ionizing radiation.

DISCLOSURE

Technical Problem

It is an object of the present invention to a method for detecting a gene sensitive to a low level of ionizing radiation, and a gene detected by the method.

Technical Solution

In order to accomplish the above objects, the present invention provides a method for detecting a gene that is sensitive to a low level of ionizing radiation and is identified in a cancer-induced individual and verified using a normal individual, the method including the steps of I) irradiating an AKR/J mouse and an ICR mouse with a low level of radiation; II) extracting thymi from the AKR/J mice and the ICR mice; subjecting the thymi to microarray analysis; IV) selecting a glucose metabolism-related gene from the microarray analysis; and V) amplifying the gene and measuring the expression level of the gene.

The present invention also provides a marker for diagnosing a radiation-sensitive or radiation-induced cancer, the marker including the nucleotide sequence of a glucose metabolism-related gene selected from the group consisting of IRS1 (NM_010570), Glut1 (MM_011400), Glut4 (NM_009204), LPK (NM_013631) and G6pc (NM_008061), which are involved in worsening of thymic cancer.

The present invention also provides a kit for diagnosing a radiation-sensitive or radiation-induced cancer, the kit including the above marker.

The present invention also provides a microarray for diagnosing a radiation-sensitive or radiation-induced cancer, the microarray including the above marker.

The present invention also provides a method for detecting a gene capable of measuring a radiation-sensitive or radiation-induced cancer, the method including the steps of I) irradiating a mammal having thymic cancer with radiation; II) bringing a test substance into contact with a thymic tissue extracted from the irradiated mammal; and III) measuring, from the thymic tissue, a change in the expression of a glucose metabolism-related gene selected from the group consisting of IRS1 (NM_010570), Glut1 (MM_011400), Glut4 (NM_009204), LPK (NM_013631) and G6pc (NM_008061), which are involved in worsening of thymic cancer.

Hereinafter, the present invention will be described in detail.

Many studies on the effects of radiation on cancer development among the effects of radiation on the human body have been conducted, but it was difficult to explain various responses of the body to radiation (responses of genes to radiation), because these studies were performed using cancer cells, gene-modified cell lines or general mice. Particularly, the profile of glucose metabolism-related genes sensitive to ionizing radiation in individuals has not yet been identified, and the functions of these genes have not been explained. Accordingly, the present invention is intended to (1) identify the profile of glucose metabolism-related genes that are expressed specifically in thymus and sensitive to a low level of radiation, and analyze the functions of the genes, after irradiating a low level (0.7 mGy/hr) of radiation (cancer development stimulator) to normal ICR mice and AKR/J mice that develop thymic cancer, and 2) diagnose the stage of development of thymic cancer using the profile of glucose metabolism-related genes.

The present invention provides a method for detecting a gene that is sensitive to a low level of ionizing radiation and is identified in a cancer-induced individual and verified using a normal individual, the method including the steps of I) irradiating an AKR/J mouse and an ICR mouse with a low level of radiation; II) extracting thymi from the AKR/J mice and the ICR mice; subjecting the thymi to microarray analysis; IV) selecting a glucose metabolism-related gene from the microarray analysis; and V) amplifying the gene and measuring the expression level of the gene.

In the inventive method for detecting a gene sensitive to a low level of ionizing radiation, irradiating the mouse with the low level of radiation is preferably performed by irradiating gamma radiation (Cs-137) at a dose rate of 0.7 mGy/hr to a final dose of 1.7 Gy. The method according to the present invention is preferably used for preparation of a kit for diagnosing thymic cancer, evaluation of the degrees of progression and treatment of cancer in a cancer patient, evaluation of the relationship between radiation exposure of industrial and medical workers and cancer development, evaluation of the causal relation between radiation and cancer development, biological evaluation of radiation exposure dose, or evaluation of the degrees of development and progression of thymic cancer caused by a low level of radiation.

In addition, the inventive method for detecting a gene sensitive to a low level of ionizing radiation, the cancer is preferably thymic cancer, and extracting the thymi in step II) is preferably performed at a time point when the mouse starts to die of the cancer.

Furthermore, in the inventive method for detecting a gene sensitive to a low level of ionizing radiation, the glucose metabolism-related gene is preferably selected from the group consisting of IRS1 (NM_010570), Glut1 (MM_011400), Glut4 (NM_009204), LPK (NM_013631) and G6pc (NM_008061). Preferably, the IRS1 (NM_010570) is amplified using primers having sequences set forth in SEQ ID NOS: 1 and 2; the Glut1 (MM_011400) gene is amplified using primers having sequences set forth in SEQ ID NOS: 3 and 4; the Glut4 (NM_009204) gene is amplified using primers having sequences set forth in SEQ ID NOS: 5 and 6; the LPK (NM_013631) gene is amplified using primers having sequences set forth in SEQ ID NOS: 7 and 8; and the G6pc (NM_008061) gene is amplified using primers having sequences set forth in SEQ ID NOS: 9 and 10.

In step IV) of selecting the glucose metabolism-related gene from the microarray analysis, a gene overexpressed or underexpressed in the cancer-induced individual after irradiation compared to in the cancer-induced individual before irradiation is detected by microarray analysis, and then verified using primers having sequences of SEQ ID NOS: 1 to 10, and the overexpressed or underexpressed gene is identified by performing a search for the function thereof. The microarray analysis is described in the Examples below, and a search for the function of the gene was performed in the Examples through the DAVID bioinformatics database and (apps1.niaid.nih.gov) and the PubMed database (www.ncbi.nlm.nih.gov), but is not limited thereto.

As used herein, "gene sensitive to a low level of radiation" refers to a gene that is differentially overexpressed or underexpressed in a cancer-induced individual after radiation compared to before irradiation. In other words, the gene refers to a gene whose expression pattern is changed by stimulation with radiation, and it may be a target gene associated with a specific cancer, that is, an oncogene or a tumor suppressor gene. When this cancer-specific gene is detected, a molecular mechanism for radiotherapy of cancer patients can be established, which can contribute to an increase in the effect of radiotherapy, and a platform for the development of agents or methods for treating cancer at the biomolecular level can be provided by screening novel oncogenes or tumor suppressor genes and regulating the expression thereof.

The present invention also provides a marker for diagnosing a radiation-sensitive or radiation-induced cancer, the marker including the nucleotide sequence of a glucose metabolism-related gene selected from the group consisting of IRS1 (NM_010570), Glut1 (MM_011400), Glut4 (NM_009204), LPK (NM_013631) and G6pc (NM_008061), which are involved in worsening of thymic cancer.

The present invention also provides a kit for diagnosing a radiation-sensitive or radiation-induced cancer, the kit including the above marker.

The present invention also provides a microarray for diagnosing a radiation-sensitive or radiation-induced cancer, the microarray including the above marker.

The present invention also provides a method for detecting a gene capable of measuring a radiation-sensitive or radiation-induced cancer, the method including the steps of I) irradiating a mammal having thymic cancer with radiation; II) bringing a test substance into contact with a thymic tissue extracted from the irradiated mammal; and measuring, from the thymic tissue, a change in the expression of a glucose metabolism-related gene selected from the group consisting of IRS1 (NM_010570), Glut1 (MM_011400), Glut4 (NM_009204), LPK (NM_013631) and G6pc (NM_008061), which are involved in worsening of thymic cancer.

In the present invention, AKR/J mice (models for thymic cancer research) and healthy ICR mice were irradiated with a low level (0.7 mGy/hr) of gamma radiation (Cs-137), and thymi were extracted at a time point (day 100) when the AKR/J mice started to die of thymic cancer. The extracted thymi were analyzed by microarray analysis, and then glucose metabolism-related genes that responded sensitively to the low level of radiation (0.7 mGy/hr) were selected through the DAVID bioinformatics database, and subjected to nucleic acid amplification, and the expression levels thereof were measured.

As a result, five genes (IRS1, Glut1, Glut4, LPK and G6pc), which responded sensitively to the low level of radiation (0.7 mGy/hr) and are important in glucose metabolism, were screened in the present invention, and the functions of the glucose metabolism-related genes (IRS1, Glut1, Glut4, LPK and G6pc) that responded sensitively to the low level of radiation (0.7 mGy/hr) were elucidated. In addition, the glucose metabolism-related genes that responded sensitively to the low level of radiation could be consistently observed by extracting thymi at day 100 when death caused by thymic cancer was observed.

Therefore, the present invention may be used to: (1) identify the profile of genes for development of a kit for diagnosing thymic cancer; (2) identify a marker for evaluating the relation of cause and effect of cancer development in industrial and medical workers who live in environments having a low level of radiation; (3) identify the profile of genes for information, which enable the diagnosis of cancer development in cancer patients and allow a cancer therapeutic method to be established; (4) identify a marker for evaluating the causal relation between radiation exposure and the development of thymic cancer; 5) identify a novel gene marker that may be widely used for biological evaluation of a low level of radiation exposure; and (6) understand ionizing radiation-sensitive glucose metabolism signaling that may be used as a target therapy for a low level of radiation exposure.

Advantageous Effects

The method for detecting a gene sensitive to a low level of ionizing radiation as described above may be used to establish the profile of glucose metabolism-related marker genes sensitive to a low level (0.7 mGy/hr) of radiation in order to prepare a kit for diagnosing thymic cancer, and may provide a glucose metabolism-related marker gene sensitive to a low level (0.7 mGy/hr) of radiation, which can be used to evaluate the degrees of progression and progression of cancer in cancer patients. Also, the method according to the present invention may provide a glucose metabolism-related marker gene sensitive to a low level (0.7 mGy/hr) of radiation, which can be used to evaluate the relationship between the radiation exposure of industrial and medical workers and cancer development. Further, it may provide a glucose metabolism-related marker sensitive to a low level of radiation, which can be used to evaluate the causal relation between radiation and cancer development. In addition, it may provide a novel marker that can be used for biological evaluation of radiation exposure dose. Also, it may provide a glucose metabolism-related marker that can be used to evaluate the degrees of development and progression of thymic cancer caused by a low level (0.7 mGy/hr) of radiation, and the effect of low-degree radiation on the suppression of thymic cancer.

MODE FOR INVENTION

Figure 1:
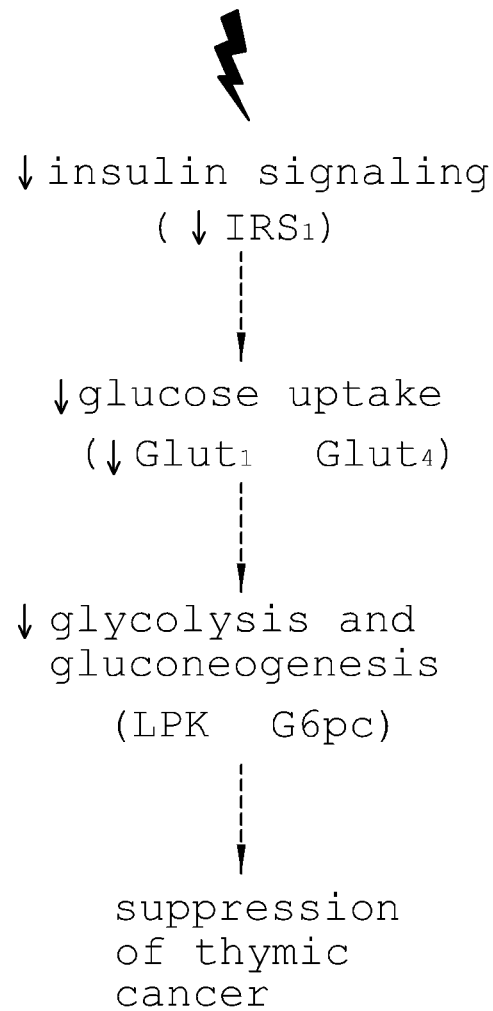
FIG. 1 schematically shows the functions of glucose metabolism-related genes that suppress thymic cancer upon irradiation with a low level (0.7 mGy/hr) of radiation.

Hereinafter, the present invention will be described in further detail with reference to examples. It is to be understood, however, that these examples are for illustrative purposes only and are not intended to limit the scope of the present invention.

Example 1

6-Week-old female AKR/J mice (models for thymic cancer research) and 6-week-old female ICR mice were purchased from SLC Co., Ltd. (Japan). A low level of radiation ($^{137}$Cs) was irradiated to the AKR/J mice using a gamma-ray generator (IBL 147C, CIS bio international, France) at a dose rate of 0.7 mGy/hr so as to reach a final dose of 4.5 Gy. After completion of irradiation with the low level of radiation, the mice were transferred into a sterilized housing system shielded from radiation, and were housed therein for 100 days while the observation of development of thymic cancer was performed. For gene analysis, under the same experimental conditions, normal mice (ICR mice) housed separately from the AKR/J mice were irradiated with a low level of radiation (0.7 mGy/hr). After 100 days, thymi were extracted from the mice and frozen rapidly in liquid nitrogen, after which gene analysis was performed.

To confirm the results, the genes were subjected to nucleic acid amplification. Specifically, the thymi extracted from the AKR/J and ICR mice irradiated with the low level of radiation (0.7 mGy/hr) were analyzed by a microarray, and glucose metabolism-related genes that responded sensitively to the low level of radiation were amplified using the primers shown in Table 1 below in order to measure the expression levels thereof.

TABLE 1

| Gene No. | Gene name | Forward (5'→3') | Reverse (5'→3') |
| --- | --- | --- | --- |
| NM_010570 | IRS1 | GGTGCAGCAGATCTGGATAA (SEQ ID NO 1) | GGTCTTCTGATGGGAAATGG (SEQ ID NO 2) |
| NM_011400 | Glut1 | ATCTTCGAGAAGGCAGGTGT (SEQ ID 3) | ACAAACAGCGACACCACAGT (SEQ ID NO 4) |
| NM_009204 | Glut4 | AGAGAGCGTCCAATGTCCTT (SEQ ID NO 5) | ACAGCATTGATGCCTGAGAG (SEQ ID NO 6) |
| NM_013631 | LPK | TGATCACTAAGGCTCGACCA (SEQ ID NO 7) | GGTCTCTCCAGACAGCATGA (SEQ ID NO 8) |
| NM_008061 | G6pc | TCCTCTTTCCCATCTGGTTC (SEQ ID NO 9) | TCCACTTGAAGACGAGGTTG (SEQ ID NO 10) |

After irradiation of the AKR/J and ICR mice with the low level of radiation (0.7 mGy/hr), the mice were housed, and thymi were extracted from the mice at a time point (day 100) when the AKR/J mice started to die of thymic cancer. The extracted thymi were microarrayed, and glucose metabolism-related genes that responded sensitively to the low level of radiation were selected, and then subjected to nucleic acid amplification, and the expression levels thereof were measured. As a result, it was shown that, in the mice irradiated with the low level of radiation, glucose metabolism-related genes (IRS1, Glut1, Glut4, LPK and G6pc) responded sensitively to the low level of radiation. The results are shown in Table 2 below.

TABLE 2

| Gene | | Microarray | | Quantitative nucleic amplification | |
|---|---|---|---|---|---|
| Gene No. | name | ICR mice | AKR/J mice | ICR mice | AKR/J mice |
| NM_010570 | IRS1 | 0.8 | 1.6 | 1.3 ± 0.1 | 1.0 ± 0.2 |
| NM_011400 | Glut1 | 1.0 | 1.1 | 2.3 ± 0.5 | 1.3 ± 0.4 |
| NM_009204 | Glut4 | 0.4 | 1.8 | 1.2 ± 0.1 | 1.1 ± 0.1 |
| NM_013631 | LPK | 1.0 | 1.4 | 2.4 ± 0.9 | 3.9 ± 1.9 |
| NM_008061 | G6pc | 0.8 | 0.7 | 1.4 ± 0.4 | 2.7 ± 0.6 |

*Expression fold value ± SD

FIG. 1 schematically shows the functions of glucose metabolism-related genes that worsen thymic cancer due to irradiation with a low level of radiation (0.7 mGy/hr). As can be seen therein, the low level of radiation reduced the expression of insulin signaling gene (IRS1), glucose uptake genes (Glut1 and Glut4), glycolysis gene (LPK) and gluconeogenesis gene (G6pc), and suppressed thymic cancer.

Figure 2:
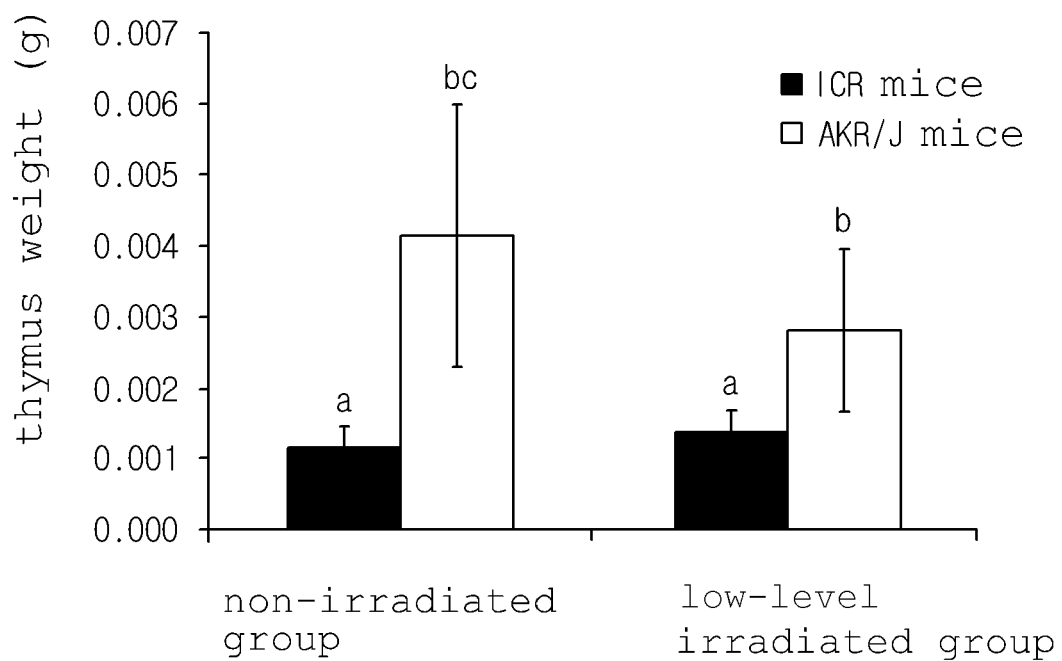
FIG. 2 is a graph showing the results obtained by irradiating AKR/J mice with a low level (0.7 mGy/hr) of radiation, and measuring the weight of thymi of the mice at a time point (day 100) when the mice started to die of thymic cancer during their housing, in order to analyze the responses of glucose metabolism-related genes sensitive to radiation based on the thymus weight.

FIG. 2 shows FIG. 2 is a graph showing the results obtained by irradiating AKR/J mice with a low level (0.7 mGy/hr) of radiation, and measuring the weight of thymi of the mice at a time point (day 100) when the mice started to die of thymic cancer during their housing, in order to analyze the responses of glucose metabolism-related genes sensitive to radiation based on the thymus weight. According to the present invention, glucose metabolism-related genes that respond sensitively to a low level of radiation can be consistently measured by extracting thymi in an early stage of cancer development in which mice start to die of thymic cancer, and comparing the weights of the extracted thymi.

The invention claimed is:

1. A method for detecting a gene sensitive to an ionizing radiation, the method comprising the steps of:
   irradiating a cancer-induced AKR/J mouse and an ICR mouse with a gamma radiation at a dose rate of 0.7 mGy/hr to a final dose of 1.7 Gy;
   extracting thymi from the AKR/J mouse and the ICR mouse;
   subjecting the thymi to a microarray analysis;
   selecting an IRS1 gene as a glucose metabolism-related gene from the microarray analysis; and
   amplifying the IRS1 gene and measuring an expression level of the gene.

2. The method of claim 1, wherein the cancer is thymic cancer.

3. The method of claim 1, further comprising the step of extracting the thymi at a time point when the mouse starts to die of the cancer.

4. The method of claim 1, wherein the step of amplifying the IRS1 gene uses primers having sequences set forth in SEQ ID NOS: 1 and 2.

\* \* \* \* \*